(12) United States Patent
Nguyen et al.

(10) Patent No.: US 9,744,260 B2
(45) Date of Patent: *Aug. 29, 2017

(54) TIMING CONTROLLED IN-SITU CROSS-LINKING OF HALYURONIC ACID DURING INJECTION

(71) Applicants: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

(72) Inventors: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

( * ) Notice: Subject to any disclaimer, the term of this patent is extended or adjusted under 35 U.S.C. 154(b) by 240 days.

This patent is subject to a terminal disclaimer.

(21) Appl. No.: 14/255,956

(22) PCT Filed: Apr. 12, 2013

(86) PCT No.: PCT/VN2013/000001
§ 371 (c)(1),
(2) Date: Apr. 18, 2014

(87) PCT Pub. No.: WO2014/169298
PCT Pub. Date: Oct. 16, 2014

(65) Prior Publication Data
US 2016/0015858 A1    Jan. 21, 2016

(51) Int. Cl.
*A61L 27/20* (2006.01)
*A61L 27/16* (2006.01)
*A61L 27/50* (2006.01)
*A61L 27/52* (2006.01)
*A61L 27/54* (2006.01)
*A61F 2/12* (2006.01)
*A61L 27/22* (2006.01)
*A61F 2/00* (2006.01)
*A61L 27/36* (2006.01)
*A61L 27/58* (2006.01)

(52) U.S. Cl.
CPC ............ *A61L 27/20* (2013.01); *A61F 2/0059* (2013.01); *A61F 2/12* (2013.01); *A61L 27/16* (2013.01); *A61L 27/222* (2013.01); *A61L 27/36* (2013.01); *A61L 27/50* (2013.01); *A61L 27/502* (2013.01); *A61L 27/52* (2013.01); *A61L 27/54* (2013.01); *A61L 27/58* (2013.01); *A61F 2230/0071* (2013.01); *A61F 2250/0003* (2013.01); *A61L 2300/204* (2013.01); *A61L 2300/222* (2013.01); *A61L 2300/402* (2013.01); *A61L 2300/416* (2013.01); *A61L 2400/06* (2013.01); *A61L 2400/18* (2013.01); *A61L 2430/04* (2013.01); *A61L 2430/34* (2013.01)

(58) Field of Classification Search
CPC ......... A61K 21/20; A61K 27/16; A61K 21/50
See application file for complete search history.

(56) References Cited

U.S. PATENT DOCUMENTS

| 4,538,920 A | 9/1985 | Drake |
| 5,219,360 A | 6/1993 | Georgiade |
| 2006/0147492 A1* | 7/2006 | Hunter ................... A61B 17/11 424/426 |
| 2007/0212385 A1 | 9/2007 | David |

* cited by examiner

*Primary Examiner* — Craig Ricci
*Assistant Examiner* — Christopher R Stone
(74) *Attorney, Agent, or Firm* — Tran & Associates

(57) ABSTRACT

Systems and methods are disclosed for cosmetic augmentation by forming a biocompatible cross-linked polymer having a multi-phase mixture with a time release catalyst; injecting the mixture into a patient as a viscous fluid; after injection, activating the catalyst to cross-link the polymer after a predetermined period after injection into a patient; and augmenting soft tissue with the biocompatible cross-linked polymer.

24 Claims, 5 Drawing Sheets

| forming a biocompatible cross-linked polymer having a multi-phase mixture with a time release catalyst (702) |
|---|
| injecting the mixture into a patient as a viscous fluid (704) |
| after injection, activating the catalyst to cross-link the polymer after a predetermined period after injection into a patient (706) |
| augmenting soft tissue with the biocompatible cross-linked polymer (708) |

FIG. 5

| Forming a cross-linked filler composition having a biocompatible, biodegradable, nontoxic properties, the filler composition having a predetermined radiolucency greater than silicone or saline radiolucency (802) |
|---|
| Injecting the mixture as separate phases into the body and mixing the mixture during the injection process to cause cross-linking of the multiphase mixture (803) |
| Introducing the filler composition into a shell or an envelope of a soft tissue human implant prior to or during implantation of the shell or envelope into a lumen in a human body (804) |
| After injection, activating the catalyst to cross-link the polymer after a predetermined period after injection into a patient (810) |

FIG. 6

TIMING CONTROLLED IN-SITU CROSS-LINKING OF HALYURONIC ACID DURING INJECTION

This application claims priority to Provisional Application Ser. 61/722,221 filed Nov. 4, 2012, and to PCT Application Serial PCT/VN2013/000001 filed Apr. 12, 2013, PCT/VN2013/000002 filed Apr. 12, 2013, PCT/VN2013/000003 filed on Apr. 12, 2013, PCT/VN2013/000004 filed Apr. 12, 2013, and PCT/VN2012/000008 filed Dec. 17, 2012, the contents of which are incorporated by reference.

BACKGROUND

The present invention relates to biodegradable hyaluronic acid filler compositions for soft tissue implants such as dermal fillers or breast, butt, or body implants.

Young, healthy-looking skin contains an abundance of a naturally hydrating substance called hyaluronic acid (HA). But as people age, sunlight and other factors can reduce the amount of HA in their skin. The lack of HA causes skin to lose structure and volume, creating unwanted facial wrinkles and folds—like those parentheses lines around the nose and mouth. Injectable dermal implants are a popular solution to a wide variety of facial contour defects from lip augmentation to plumping up depressed scars. Often used as tissue replacement for victims of serious accidents, injectable dermal implants are very effective in cosmetic surgery procedures such as lip augmentation and scar removal. Using a dermal filler is a safe and effective way to replace the HA the skin has lost, bringing back its volume and smoothing away facial wrinkles and folds.

In a parallel trend, millions of women have undergone breast, butt, or body augmentation and reconstruction in the past few decades. Most women choose augmentation to enhance the size and shape of one or both breast, butt, or bodys for personal or aesthetic reasons. In contrast, women who undergo a reconstruction procedure want to reconstruct a breast, butt, or body that has been removed, typically for health reasons, such as tumor removal. The reconstruction procedure may vary from a modified radical mastectomy (removal of the underlying muscle as well as the breast, butt, or body part), to a simple mastectomy (removal of one breast, butt, or body part), to a bilateral mastectomy (removal of both breast, butt, or body parts) or to a lumpectomy (removal of a portion of the breast, butt, or body part). In either augmentation or reconstruction, the modality intimates the surgical implantation of a breast, butt, or body prosthesis (implant).

Conventional implants for treating breast, butt, or body augmentation or reconstruction include a shell or envelope that is filled with a filler composition, for example, silicone gel, saline solution, or other suitable filler. It is desirable that the filler have lubricating properties to prevent shell abrasion, remain stable over long periods of time, be non-carcinogenic and non-toxic, and have physical properties to prevent skin wrinkling, capsular contracture formation, and implant palpability.

In response to the failures of saline and silicone-gel implants, there have been a number of attempts to make a prosthesis filled with a non-toxic filler that that mimics the shape and feel of a natural breast, butt, or body provided by silicone-gel yet is safe to the immune system like saline. Other attempts to provide a safe filler material include polyethylene glycol. However, the triglyceride oil or honey fails to provide an implant that is aesthetically pleasing and also duplicates the touch and feel of a natural breast, butt, or body due to the low viscosity of the fillers. Due to the limited options and the inadequacy of current fillers to achieve the desired results, there is a need for safe and efficacious fillers.

In one trend, hyaluronic acid (HA) has been steadily gaining popularity in the area of aesthetic medicine because of its ubiquity and biocompatibility. HA has been limited to small areas such as nasal labial folds, lips and glabella lines to name a few. However, if the HA is cross linked in-vitro, the non-Newtonian nature of the HA cross linked gel makes it very difficult to augment larger anatomical spaces in a minimally invasive fashion.

SUMMARY

In one aspect, systems and methods are disclosed for cosmetic augmentation by by forming a biocompatible cross-linked polymer having a multi-phase mixture with a time release catalyst; injecting the mixture into a patient as a viscous fluid; after injection, activating the catalyst to cross-link the polymer after a predetermined period after injection into a patient; and augmenting soft tissue with the biocompatible cross-linked polymer.

Examples of time triggered materials that can protect one of the reactant to keep the reaction from initiating are low/medium water soluble biocompatible materials such as:
  Raw HA
  Hydroxy propyl methelcellulose (HPMC), cellulose
  Polysaccharides
  Hydrogels (HEMA, acrylamide)
  Collagen These or one these of materials would be coated or encapsulated over the reactant. When the reactant is exposed because the protection coating had all been dissolved then the reaction will kick off.

The protection material may also be longer lasting materials such as polyvinyl alcohol and various levels of hydrolysis.

Applying the protection material over the reactant may be done by various processes. The requirements are an understand of the interactions of the reactant and the protection material. The electronic charges, polarities, dipoles and structural orientation are key variables in determining how well the protection material would function. The purpose is the orientation of the protection material to keep the reactants from finding each other and kick off the reaction. Some of the methods to apply the protection materials are:
  Spray drying
  Fluidized bed coating
  Solvent evaporation
  Emulsification In one implementation, the process cross links HA using conventional methods and commonly used cross linkers by protecting one of the reactant while still participating with all the other reactants in getting a homogeneous mixing for uniform physical properties. If possible, the cross linker should be considered for protect first because there is less quantity of it. The timing component process is the duration until the protection had worn off.

In another aspect, systems and methods are disclosed for breast, butt, or body implants by forming a biocompatible cross-linked polymer having a multi-phase mixture with a predetermined controlled release of selected pharmaceutical substance to modulate soft tissue response to the polymer; injecting the mixture into a patient and during or after injection, cross-linking the polymer in the patient; filling a semi-permeable shell with the pharmaceutical substance; and augmenting soft tissue with the biocompatible cross-linked polymer.

Advantages of the system may include one or more of the following. The flow properties are tailored for injection through a small bore needle. The system has greater flexibility to control physical properties of the final gel. The final gel could be tailored to have greater cohesive strength which will resist migration to another anatomical space. The final gel durometer could be tailored to be more natural and tissue-like. The final gel could be tailored to have properties similar to surround tissue. The longevity of the final gel could be tailored to meet various anatomical location requirements (longer biodegradation or shorter depending on anatomical location). The final gel physical properties stay constant over the life time of the material.

BRIEF DESCRIPTION OF THE DRAWINGS

FIG. 5 shows an exemplary process to inject and cross-link materials using time-released catalyst.

FIG. 6 shows another exemplary process to inject and cross-link materials using time-released catalyst.

DESCRIPTION

Figure 1:
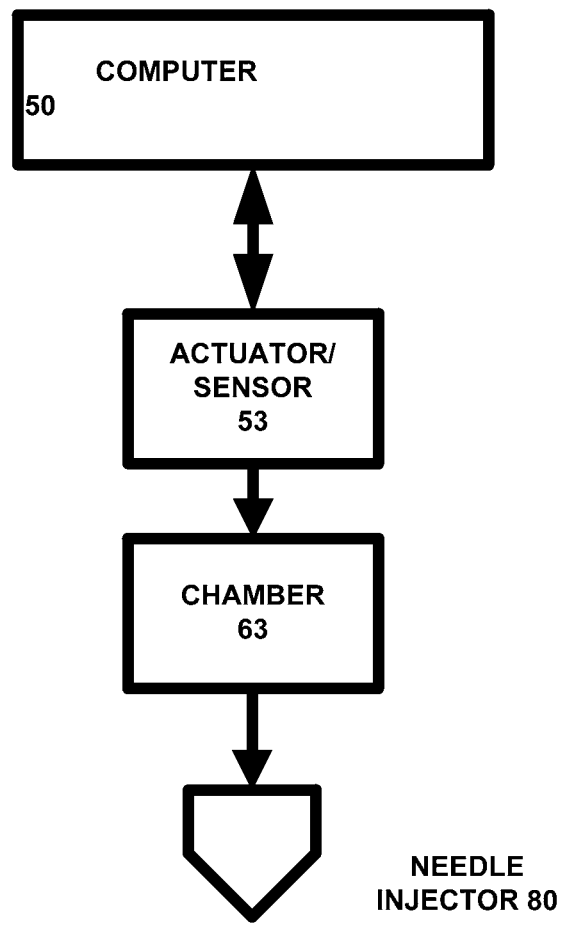
FIG. 1 shows an exemplary block diagram of a computer controlled hyaluronic acid (HA) injector system that cross-links the HA for a predetermined period after a time release catalyst is injected into the body.

FIG. 1 shows an exemplary block diagram of a hyaluronic acid (HA) injector system that cross-links the HA while the drug is injected into the body. As shown therein, a cartridge with a container 63 housing a flowable component to be mixed when desired in a static mixer. The container 63 terminates in an outlet tip from which the components mixed by the static mixer are expelled. The static mixer may be separable from and attached to the containers or chambers in a manner known per se. The containers, usually made of a plastics material, are joined by a bridge defining an outlet in which the two components are separated by an internal dividing wall to maintain the components separate and unmixed until they reach inlet of the static mixer for mixing therein. In a conventional manner, the static mixer, again usually of a plastics material, comprises a static mixer element housed in an elongate member extending from attachment to the outlet to outlet tip. Also the static mixer element comprises an axially extending serial plurality of alternating oppositely oriented helically twisted mixer blades which act in concert to efficiently and thoroughly mix the separate components as they flow through the static mixer 6 from the outlet to the outlet tip. Pistons or motorized actuators are operated simultaneously by a suitable mechanism (not shown) with the cartridge being retained by the back plate, to dispense the components simultaneously from the containers through the outlet and static mixer to the outlet tip. In this embodiment, the actuators are controlled by a computer for precise mixing and delivery as desired. In one embodiment, a plurality of outlets can be provided so that a plurality of patient areas can be injected in parallel.

Figure 2:
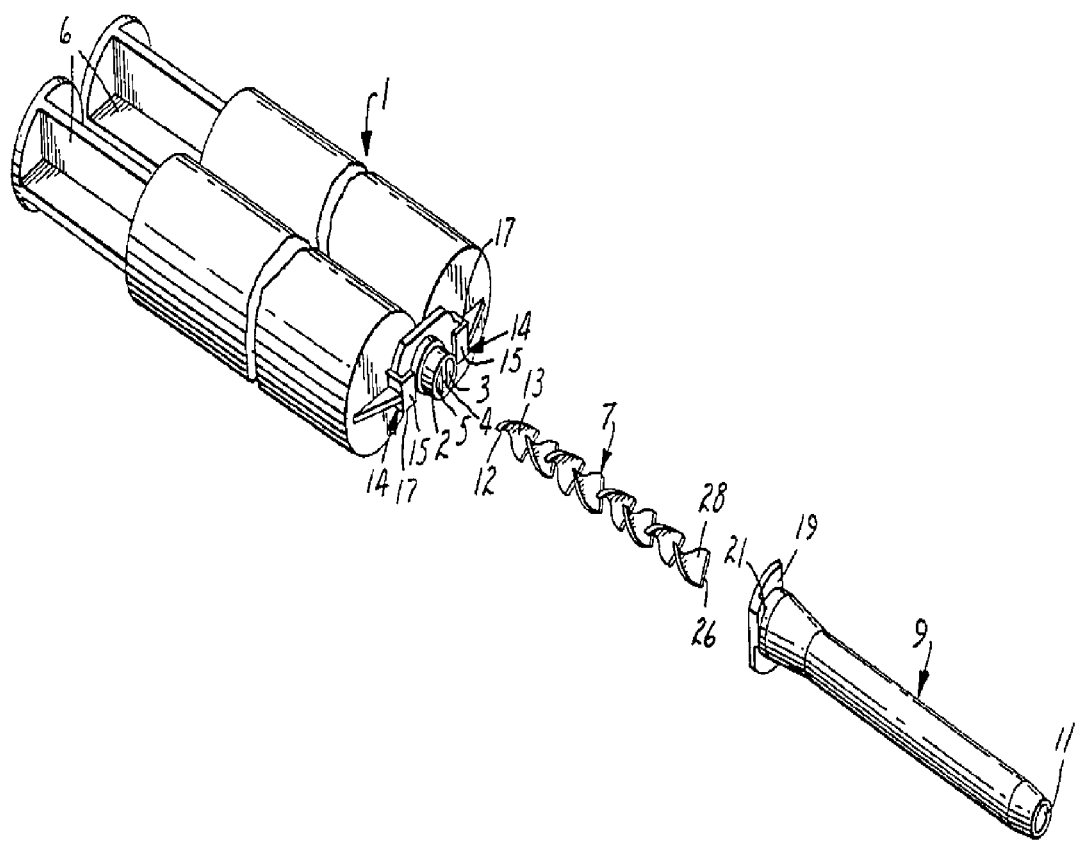
FIGS. 2-3 shows an exemplary manual hyaluronic acid (HA) injector system that cross-links the HA for a predetermined period after a time release catalyst is injected into the body.

Referring now to FIG. 2, there is shown an exploded view in perspective of a static mixing device for forming cross-linked HA as it is injected into the patient. Syringe 1 has two or three parallel internal chambers, each of which is intended to be filled with a cross-linked material such as DVS, a filler material such as hyaluronic acid, and a catalyst such as sodium bicarbonate solute. The chambers in syringe 1 are separated by barrier 4. When a pair of plungers 6 are forced into the chambers in syringe 1, the contents of the syringe exit via outlet 2 through outlet passages 3 and 5, flow through static mixing element 7 and exit conduit 9, and are intimately mixed to form a homogeneous mass which will rapidly polymerize following expulsion from outlet 11 of exit conduit 9. Static mixing element 7 is prevented from being expelled during use from the outlet end of exit conduit 9 by a suitable constriction in the inside diameter of exit conduit 9 proximate its outlet end.

In one embodiment, maximum efficiency of mixing is obtained by insuring that the inlet end 12 of the first mixing blade 13 of static mixing element 7 is generally perpendicular to the plain of contiguity between the two resin streams exiting syringe 1 through exit passages 3 and 5. Such perpendicular orientation is obtained using a locating tang in exit conduit 9, which locating tang serves to orient static mixing element 7 with respect to syringe 1.

Rotational alignment of exit conduit 9 with respect to syringe 1 is obtained using a suitable mounting means (e.g., a bayonet mount). Bayonet locking tabs 14 have locking prongs 15 and stop surfaces 17. Exit conduit 9 has locking ramps 19 and stop surfaces 21. Exit conduit 9 is mounted on syringe 1 by centering the inlet of exit conduit 9 over outlet 2 of syringe 1, while aligning exit conduit 9 so that it can be pushed between bayonet locking tabs 14. Exit conduit 9 is then inserted firmly over outlet 2, and rotated approximately 90° clockwise (as viewed from the exit end of the conduit) so that locking ramps 19 are wedged between locking prongs 15 and the main body of syringe 1, and stop surfaces 17 engage stop surfaces 21.

When so mounted, exit conduit 9 is fixably rotationally aligned with respect to syringe 1. In addition, through locating means described in more detail below, static mixing element 7 is fixably rotationally aligned with respect to exit conduit 7 and syringe 1. Static mixing element 7 and exit conduit 9 are firmly attached to syringe 1, but can be readily removed and discarded after use by rotating exit conduit 9 approximately 90° counterclockwise (as viewed from the exit end of the conduit) and pulling exit conduit 9 away from syringe 1.

Syringe 1, exit nozzle 2, exit passages 3 and 5, barrier 4, plungers 6, static mixing element 7, exit conduit 9, inlet edge 12, first mixing blade 13, bayonet locking tabs 14, and locking prongs 15 are as in FIG. 1. Static mixing element 7 is rotationally aligned within exit conduit 9 by one or more guides proximate the outlet end of exit conduit 9. Guides 24 and 25 are small inward projections in the bore of exit conduit 9, and have a "fish mouth" appearance when viewed in perspective. When viewed in isolation, locking guides 24 and 25 each resemble the nib of a fountain pen.

When static mixing element 7 is inserted into the inlet end of exit conduit 9, and pushed toward the outlet end of exit conduit 9, guides 24 and 25 serve to rotationally align static mixing element 7 within exit conduit 9. When leading edge 26 of the final mixing blade 28 of static mixing element 7 approaches the outlet end of exit conduit 9, guides 24 and 25 cause static mixing element 7 to rotate about its long axis until leading edge 26 abuts edge surface 24a of guide 24 or edge surface 25a of guide 25.

When a static mixing element is inserted sufficiently far into exit conduit 9 to strike cusp 33, the leading edge of the static mixing element is deflected by cusp 33 toward edge surface 24a or toward edge surface 24b, thereby providing the desired rotational alignment. Depending upon whether the static mixing element abuts against edge surface 24a or 24b of guide 24 (and against corresponding edge surface 25b or 25a of guide 25), the final orientation of the static mixing element will be in one of two positions, each of those positions being 180° of rotation apart from the other. Each position is equally acceptable as a means for optimizing the efficiency of the first blade of the static mixing element, since in either position the first mixing element will intersect the incoming streams of resin at an approximate right angle to the plane of contiguity between the incoming streams and subdivide the incoming streams equally.

Upon injection into the patient's body, the contents of the chambers are mixed: a first chamber containing a cross-linking material such as DVS, a second chamber containing hyaluronic acid (HA), and a third chamber containing a catalyst such as sodium bicarbonate solution.

The encapsulated time release chemicals and methods of this invention are useful in a variety of applications. The term "controlled time release" is used herein to mean that a chemical encapsulated in accordance with the preferred embodiment will release at a known rate into the HA in which it is mixed in a selected time period to cause cross-linking of the HA. While any of a great variety of chemicals can be encapsulated in accordance with this invention and used in a variety of applications, the encapsulated chemicals and methods are particularly suitable for use in cosmetic applications. Further, the encapsulated chemicals and methods of this system are particularly suitable for encapsulating hydrogels, but they also provide excellent encapsulation and time release for dry particulate solid chemicals.

It will be understood by the artisan that the bioabsorbable HA delivery devices discussed herein may be formed out of hydrogels and/or polymer blends of glycolide and/or lactide homopolymer, copolymer and/or glycolide/lactide copolymer and polycaprolactone copolymers and/or copolymers of glycolide, lactide, poly (L-lactide-co-DL-lactide), caprolactone, polyorthoesters, polydioxanone, trimethylene carbonate and/or polyethylene oxide or any other bioabsorbable material. Similarly, it will be further understood that therapeutic agents suitable for timed release by the various embodiments of the HA delivery device described herein include antibiotic compositions, analgesics, lactoferrin and any other compositions effective for reducing infection and/or promoting healing of a wound formed at a surgical site. The therapeutic agents can include timed release or otherwise controllable properties which can be provided by the hydrogels discussed above and/or the synthetic molecular level devices referenced above or other timed release agents or mechanisms known in the art. When synthetic molecular level devices are employed, they can be turned on and off or opened and closed by various stimuli such as sound or a magnetic field or other means. Therapeutic agents and/or delivery systems employing nanotechnologies can also be employed and these can include sustained release systems and other drug delivery systems known in the art, solubility enhancement, adjuvant carriers, manufactured neurons to aid in reversal of paralysis, nano-sized therapeutic agents and the like.

The release of the catalyst from the composition may be varied or controlled, for example, by the solubility of a biologically-active agent in aqueous tissue fluids, the distribution of the bioactive agent within the matrix, the size, shape, porosity, solubility and biodegradability of the composition, the type and amount of crystallization-controlling agent and/or an additive, triggering a synthetic molecular level device and/or the like. The relative amounts of bioabsorbable/biodegradable polymer and/or hydrogel in the HA delivery device in accordance with all of the embodiments of the present invention may vary widely, depending on the rate of dissolution of the polymer and/or hydrogel (and, therefore, the rate of catalyst release) desired. The polymer and/or hydrogel composition includes the therapeutic agent in an amount effective to provide the desired level of biological, physiological, pharmacological and/or therapeutic effect in the patient. There is generally no critical upper limit on the amount of the therapeutic agent included in the composition. The only limitation is a physical limitation for advantageous application (i.e., the therapeutic agent should not be present in such a high concentration that the consistency and handling of the composition is adversely affected). The lower limit of the amount of therapeutic agent incorporated into the composition will depend on the activity of the therapeutic agent and the period of time desired for treatment.

A variety of antibiotic drugs can be used in the implants to treat or prevent infection. Suitable antibiotics include many classes, such as aminoglycosides, penicillins, semi-synthetic penicillins, cephalosporins, doxycycline, gentamicin, bacitracin, vancomycin, methicillin, cefazolin and quinolines. Clindamycin has been reported to release readily from composites comprising polylactic acid. Anti-inflammatory agents such as hydrocortisone, prednisone, and the like may comprise the therapeutic agent. Substances useful for promoting growth and survival of cells and tissues or augmenting the functioning of cells, as for example, a nerve growth promoting substance such as a ganglioside, a nerve growth factor; a hard tissue growth promoting agent such as an osteoinductive growth factor, are also possible therapeutic agents suitable for incorporation within a modular drug delivery device of the present invention. The protein lactoferrin, an iron scavenger, has recently been shown to prevent the buildup of "biofilms" comprising bacterial colonies. The incorporation of lactoferrin into an implantable modular drug delivery system may be useful for preventing the formation of harmful biofilms at a surgical site.

The rate of release of a therapeutic agent from the modular drug delivery device generally depends on the concentration of the therapeutic agent in the composition and the choice of bioabsorbable polymer and/or hydrogel. For a particular polymer and/or hydrogel, the rate of release may further be controlled by the inclusion of one or more additives that function as a release rate modification agent, and by varying the concentration of that additive. The release rate modification additive may be, for example, an organic substance which is water-soluble or water insoluble. Useful release rate modification agents include, for example, fatty acids, triglycerides, other like hydrophobic compounds, organic solvents, plasticizing compounds and synthetic molecular level devices.

The inner content 6 of the implant is a composition that is composed mainly of hyaluronic acid. The term "hyaluronic acid" is used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs. The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term. HA can also be defined as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein. More details on how to make the HA are discussed in commonly owned, co-pending application Ser. No. 13353316, filed Jan. 18, 2012, and entitled "INJECTABLE FILLER," the content of which is incorporated by reference.

Figure 3:
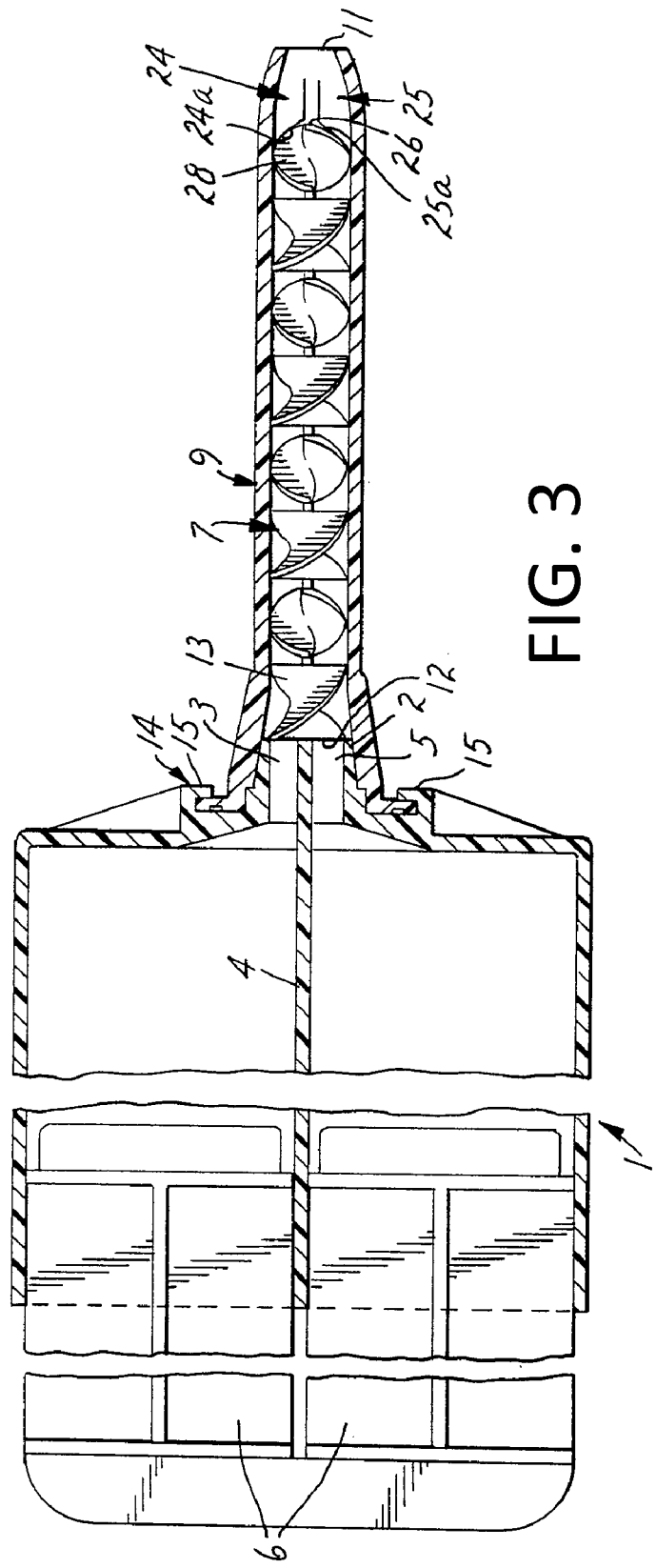
Figure 4:
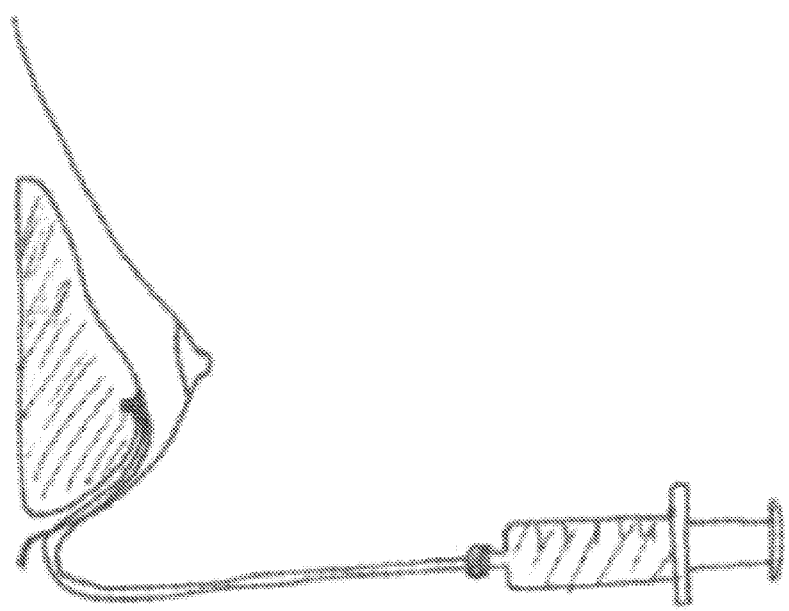
FIG. 4 shows an exemplary breast, butt, or body implant delivery system.

The injectors of FIG. 1 or FIGS. 2-3 can be used to inject HA for dermal filling or for filling a breast, butt, or body implant, as shown in FIG. 4.

FIG. 5 shows an exemplary process to inject and cross-link materials at the same time. The process includes forming a biocompatible cross-linked polymer having a multi-phase mixture with a time release catalyst (702). Next, the process injects the mixture into a patient as a viscous fluid (704). After injection, the catalyst is activated to cross-link the polymer after a predetermined period after injection into a patient (706). Finally, the cross-linked polymers are used for augmenting soft tissue with the biocompatible cross-linked polymer (708).

FIG. 6 shows another exemplary process to inject and cross-link materials at the same time. The process includes forming a cross-linked filler composition having a biocompatible, biodegradable, nontoxic properties, the filler composition having a predetermined radiolucency greater than silicone or saline radiolucency (802). The process also injects the mixture as separate phases into the body and mixing the mixture during the injection process to cause cross-linking of the multiphase mixture (803). The filler composition with HA and cross linking materials is introduced into a shell or an envelope of a soft tissue human implant prior to or during implantation of the shell or envelope into a lumen in a human body (804). The cross-linking of the filler composition occurs, and the cross linking reaction occurs outside the shell/envelope or in-situ inside the shell/envelope (810).

Examples of time triggered materials that can protect one of the reactant to keep the reaction from initiating are low/medium water soluble biocompatible materials such as:
Raw HA
Hydroxy propyl methelcellulose (HPMC), cellulose
Polysaccharides
Hydrogels (HEMA, acrylamide)
Collagen These or one these of materials would be coated or encapsulated over the reactant. When the reactant is exposed because the protection coating had all been dissolved then the reaction will kick off.

The protection material may also be longer lasting materials such as polyvinyl alcohol and various levels of hydrolysis.

Applying the protection material over the reactant may be done by various processes. The requirements are an understand of the interactions of the reactant and the protection material. The electronic charges, polarities, dipoles and structural orientation are key variables in determining how well the protection material would function. The purpose is the orientation of the protection material to keep the reactants from finding each other and kick off the reaction. Some of the methods to apply the protection materials are:
Spray drying
Fluidized bed coating
Solvent evaporation
Emulsification In one implementation, the process cross links HA using conventional methods and commonly used cross linkers by protecting one of the reactant while still participating with all the other reactants in getting a homogeneous mixing for uniform physical properties. If possible, the cross linker should be considered for protect first because there is less quantity of it. The timing component process extends the duration until the protection had worn off The cross-link time resulting from the use of a stable, non-aqueous suspension of a delayed cross-linker according to the preferred embodiment may be controlled by varying any one or all of the following:
1) the cross linking compound used,
2) the particle size of the HA in suspension,
3) the pH of the fluid containing the HA,
4) the concentration (i.e., loading) of the HA suspension,
5) the temperature of the solution.

Illustratively, when used under similar conditions, the type of molecular weight of the HA compound may be employed effectively to control the exact cross-linking time of the water-soluble solution. More particularly, suspensions of larger molecular weight HA cross-link more slowly than suspensions of low molecular weight acid.

With respect to the particle size of the suspended halyuronic acid, as particle size increases, the time required for the cross-linking of a water-soluble polymer solution increases. Conversely, as the particle size decreases, the time required for the cross-linking of a water soluble decreases.

The pH of the water soluble polymer solution prior to its cross-linking may be used to control cross-link time. The pH of the water soluble polymer solution affects the solubility rate of the stable, non-aqueous suspension of a delayed cross-linker. Specifically, as the pH of the water soluble polymer solution increases, the solubility rate of the cross-linker suspension increases if the suspension contains a majority of HA particles, whereas the solubility rate of the cross-linker suspension decreases if the suspension contains a majority of borax particles. Conversely, as the pH of the water soluble polymer solution decreases, the solubility rate of the cross-linker suspension decreases if the suspension contains a majority of boric acid particles, whereas the solubility rate of the cross-linker suspension increases if the suspension contains a majority of HA particles.

Both the concentration (i.e., loading) of the stable, non-aqueous suspension of a delayed HA cross-linker in the water soluble polymer solution and the content of the cross-linker suspension affect the cross-link time of a water soluble polymer solution similarly. As either the concentration of the suspension of delayed HA cross-linker in the water-soluble polymer solution or the content of the cross-linker suspension increase, the cross-link time of the water soluble polymer solution decreases. Conversely, as either the concentration of the suspension of the delayed boron cross-linker in the water soluble polymer solution and the content of the cross-linker suspension decrease, the cross-link time of the water soluble polymer solution increases.

Temperature may be used to alter the cross-link time of a water soluble polymer solution. As the temperature of the water soluble polymer solution increases, its cross-link time decreases. Conversely, as the temperature of the water soluble polymer solution decreases, its cross-link time increases. Furthermore, the cross-link time of a water-soluble polymer may be increased or decreased depending upon the clay type utilized in the formulation of the stable, non-aqueous suspension of a delayed HA cross-linker.

In addition, materials such as polymeric microspheres, polymer micelles, soluble polymers and hydrogel-type materials can be used for providing protection for pharmaceuticals against biochemical degradation, and thus have shown great potential for use in biomedical applications, particularly as components of drug delivery devices. The design and engineering of biomedical polymers (e.g., polymers for use under physiological conditions) are generally subject to specific and stringent requirements. In particular, such polymeric materials must be compatible with the biological milieu in which they will be used, which often means that they show certain characteristics of hydrophilicity. They also have to demonstrate adequate biodegradability (i.e., they degrade to low molecular weight species. The polymer fragments are in turn metabolized in the body or excreted, leaving no trace). Biodegradability is typically accomplished by synthesizing or using polymers that have hydrolytically unstable linkages in the backbone. The most common chemical functional groups with this characteristic are esters, anhydrides, orthoesters, and amides. Chemical hydrolysis of the hydrolytically unstable backbone is the prevailing mechanism for the degradation of the polymer. Biodegradable polymers can be either natural or synthetic. Synthetic polymers commonly used in medical applications and biomedical research include polyethyleneglycol (pharmacokinetics and immune response modifier), polyvinyl alcohol (drug carrier), and poly(hydroxypropylmetacrylamide) (drug carrier). In addition, natural polymers are also used in biomedical applications. For instance, dextran, hydroxyethylstarch, albumin and partially hydrolyzed proteins find use in applications ranging from plasma substitute, to radiopharmaceutical to parenteral nutrition. In general, synthetic polymers may offer greater advantages than natural materials in that they can be tailored to give a wider range of properties and more predictable lot-to-lot uniformity than can materials from natural sources.

In one embodiment, the linker is a dicarboxylic acid with at least three atoms between the carbonyls and contains a heteroatom alpha to the carbonyl forming the ester, the release half-life is less than about 10 hours; when Linker is a dicarboxylic acid with at least three atoms between the carbonyls with no heteroatom alpha to the carbonyl forming the ester, the release half-life is more than about 100 hours; wherein when Linker is a dicarboxylic acid with two atoms between the carbonyls and Tether contains a nitrogen with a reactive hydrogen, the release half-life of the HA is from about 0.1 hours to about 20 hours; wherein the release half-life being measured in 0.05M phosphate buffer, 0.9% saline, pH 7.4, at 37° C.; with the proviso that the conjugate is not PHF-SA-Gly-CPT, PHF-(methyl)SA-Gly-CPT, PHF-(2,2-dimethyl)SA-Gly-CPT, PHF-(2-nonen-2-yl)SA-Gly-CPT, PHF-SA-Gly-Taxol, or PHF-SA-Gly-Illudin.

In some embodiments, the polyal is an acetal. In other embodiments, the polyal is a ketal. In some embodiments, the acetal is PHF. In some embodiments, Ri is H. In other embodiments, Ri is CH3. In some embodiments, R2 is —CH(Y)—C(O)—, wherein Y is one of the side chains of the naturally occurring amino acids. In some embodiments, R2 is an aryl group. In some embodiments, R2 is anheteroaryl group. In other embodiments, R2 is an aliphatic ring. In some embodiments, R2 is an aliphatic chain. In some embodiments, R2 is a heterocyclic aliphatic ring. In some embodiments, Ri and R2 when taken together with nitrogen to which they are attached form a ring. Other embodiments are known to those skilled in the art. For example, some embodiments are discussed in US2010/036413, the content of which is incorporated by reference.

With certain HAs, the cross linking of the HA external to the shell can cause the cross-linked gel to become hardened and thus the HA may not be inserted into the shell easily with desired properties. A reversible cross-linking system can be used in one embodiment, where the cross links will be labile at extreme pH values, and at physiological pH, the cross-links become fixed. Two product streams can enter the shell, one is the product at an altered pH state and the other is the PBS, the neutralizer.

Gelling by either bioresponsive self-assembly or mixing of binary crosslinking systems, these technologies are useful in minimally invasive applications as well as drug delivery systems in which the sol-to-gel transition aids the formulation's performance. Moreover, not only does the chemical nature of the crosslinking moieties allow these systems to perform in situ, but they contribute dramatically to the mechanical properties of the hydrogel networks. For example, reversible crosslinks with finite lifetimes generate dynamic viscoelastic gels with time-dependent properties, whereas irreversible crosslinks form highly elastic networks.

The intrinsic properties of in situ forming gels add a new dimension of flexibility to large space augmentation such as that of the breast, butt, or body and the buttock. While the silicone filled shell gives the feel and touch of native tissue, the long term health and legal complications associated of foreign body reaction and biocompatibility cannot be avoided. The over the lifetime of the implant, the fact that silicone fluid finding its way to the tissue on the outside of the shell is a kinetic eventuality. Saline filled shell has been a reluctant alternative because its feel and aesthetic affect are far from natural. The best of both worlds alternative might be found in a native material such as hyaluronic acids. The required properties might be best satisfied in an in situ crosslinked hyaluronic acid, or ex situ crosslinked hyaluronic acid or super high molecular weight linear (un-crosslinked) hyaluronic acids.

The following are examples of in situ crosslinking method for hyaluronic acids:

1. Hyaluronic acids, hydrazide and aldehyde:

Doubly crosslinked networks composed of HA microgels and crosslinked hydrogels with tunable is coelasticity in the relevant frequency range have been proposed for vocal fold healing. These partially monolithic and partially living materials feature divinylsulfone-crosslinked HA particles that have been oxidized with periodate to produce surface aldehyde functionalities.

A derivative of hyaluronic acid (HA), comprising the steps of:

1.1. forming an activated ester at a carboxylate of a glucuronic acid moiety of hyaluronic acid;

1.2. substituting at the carbonyl carbon of the activated ester formed in step 1.1

1.3. a side chain comprising a nucleophilic portion and a functional group portion; and 1.4. forming a cross-linked hydrogel from the functional group portion of the hyaluronic acid derivative in solution under physiological conditions wherein the forming of a cross-linked hydrogel is not by photo-cross-linking.

2. Hyaluronic acid, dextran by forming a hydrazine 3. Functionalization of hyaluronic acid (HA) with chemoselective groups enables in situ formation of HA-based materials in minimally invasive injectable manner. One embodiment of HA modification with such groups primarily rely on the use of a large excess of a reagent to introduce a unique reactive handle into HA and, therefore, are difficult to control. FIG. 9 shows another embodiment with a protective group strategy based on initial mild cleavage of a disulfide bond followed by elimination of the generated 2-thioethoxycarbonyl moiety ultimately affording free amine-type functionality, such as hydrazide, aminooxy, and carbazate. Specifically, new modifying homobifunctional reagents may be synthesized that contain a new divalent disulfide-based protecting group. Amidation of HA with these reagents gives rise to either one-end coupling product or to intra/intermolecular cross-linking of the HA chains. However, after subsequent treatment of the amidation reaction mixture with dithiothreitol (DTT), these cross-linkages are cleaved, ultimately exposing free amine-type groups. The same methodology was applied to graft serine residues to the HA backbone, which were subsequently oxidized into aldehyde groups. The strategy therefore encompasses a new approach for mild and highly controlled functionalization of HA with both nucleophilic and electrophilic chemoselective functionalities with the emphasis for the subsequent conjugation and in situ cross-linking. A series of new hydrogel materials were prepared by mixing the new HA-aldehyde derivative with different HA-nucleophile counterparts. Rheological properties of the formed hydrogels were determined and related to the structural characteristics of the gel networks. Human dermal fibroblasts remained viable while cultured with the hydrogels for 3 days, with no sign of cytotoxicity, suggesting that the gels described in this study are candidates for use as growth factors delivery vehicles for tissue engineering applications.

4. The gelation is attributed to the Schiff base reaction between amino and aldehyde groups of polysaccharide derivatives. In the current work, N-succinyl-chitosan (S-CS) and aldehyde hyaluronic acid (A-HA) were synthesized for preparation of the composite hydrogels.

5. Injectable hyaluronic acid (HA) hydrogels cross-linked via disulfide bond are synthesized using a thiol-disulfide exchange reaction. The production of small-molecule reaction product, pyridine-2-thione, allows the hydrogel formation process to be monitored quantitatively in real-time by UV spectroscopy. Rheological tests show that the hydrogels formed within minutes at 37° C. Mechanical properties and equilibrium swelling degree of the hydrogels can be controlled by varying the ratio of HA pyridyl disulfide and macro-cross-linker PEG-dithiol. Degradation of the hydrogels was achieved both enzymatically and chemically by disulfide reduction with distinctly different kinetics and profiles. In the presence of hyaluronidase, hydrogel mass loss over time was linear and the degradation was faster at higher enzyme concentrations, suggesting surface-limited degradation.

Other Examples include:

A. To produce a crosslinked hyaluronic acid filler composition by in-situ cross linking Using DivinylSulfone to fill a 200 mL silicone shell:
1. Hyaluronic Acid (2M Dalton) 1.5 g
2. NaOH (0.2N) 50 mL
3. Combine the two and mix until completely dissolved
4. Inject this hyaluronic acid/NaOH mixture into the silicone shell 35 μL
5. Divinylsulfone 150 μL
6. PBS (phosphate buffered saline) 150 mL
7. Thoroughly mix the PBS and DVS
8. Inject the PBS/DVS into the shell
9. Mix vigorously together for homogeneous crosslinking reaction
10. Neutralize using an appropriate amount of acid such as hydrochloric acid with the pH be monitored.
10. Use appropriately B. To produce a crosslinked hyaluronic acid filler composition by in-situ cross linking Using 1,4-butane dioldiglycidyl ether (BDDE) to fill a 200 mL silicone shell:
1. Hyaluronic Acid (2M Dalton) 2.0 g
2. NaOH (0.2N) 50 mL
3. Combine the two and mix until completely dissolved
4. Inject this hyaluronic acid/NaOH mixture into the silicone shell 40 μL
5. 1,4-butane dioldiglycidyl ether 150 μL
6. PBS (phosphate buffered saline) 150 mL
7. Thoroughly mix the PBS and BDDE
8. Inject the PBS/BDDE into the shell
9. Mix vigorously together for homogeneous crosslinking reaction
10. Neutralize using an appropriate amount of acid such as hydrochloric acid with the pH be monitored.
11. Use appropriately The viscosity of these polymers could be controlled by using its pH properties. The low viscosity region during low pH environment helps with deployment of the augmentation gel because the gel has to be delivered through a small diameter tubing. Polymers that are pH sensitive are also called polyelectrolytes. The swelling properties of polyelectrolyte networks, which can be described in terms of the swelling rate and maximum solution uptake at equilibrium, depend on the physicochemical properties of the polymers and on the composition of the surrounding medium. Polyelectrolyte gels change their conformation with the degree of dissociation which is the function of quantities such as pH value, polarity of the solvent, ionic strength and temperature of the external environment solution.

Example C

Synthesis of biocompatible and biodegradable polyelectrolyte hydrogels based on polyvinyl pyrrolidone (PVP), gelatin and hyaluronic acid (HA) using gamma irradiation polymerization technique. The example polymers of C1 and C2 at pH 5 exponentially increased their water absorption properties. The addition of PVP and gelatin were for in-vitro handling and processing ease.

C1
PVP 5 g
Hyaluronic acid 1 g
Mix well and expose the mixture to 30 kGy radiation C2
Gelatin 10 g
Hyaluronic acid 1 g
Mix well and expose the mixture to 30 kGy radiation Example D Synthesis of hyaluronic acid and polyvinyl alcohol at various respective ratios in an interpenetrating networks. The polyvinyl alcohol included in the polymer system was for ease of in-vitro handling and processing. Glutaraldehyde and hydrochloric acid were catalysts for the PVA reaction. The 1-ethyl-(3-3-dimethylaminopropyl) carbodiimide hydrochloride was the catalyst for the hyaluronic acid reaction. The two materials independently crosslinked at their primary structure levels while their secondary structures intertwined to create interpenetrating polymer networks. Examples D1, D2 and D3, at pH 4 exponential changed their water absorption properties.

D1
  Hyaluronic acid 3 g
  Polyvinyl alcohol 1 g
D2
  Hyaluronic acid 1 g
  Polyvinyl alcohol 1 g
D3
  Hyaluronic acid 1 g
  Polyvinyl alcohol 3 g Another preferred embodiment is filling a silicone shell with cross-linked hyaluronic acid material. This method required a high sheer mixer. The HA is cross linked using available cross-linkers such as divinylsulfone, 1, 4-butane dioldiglycidyl ether in the presence of 0.1M sodium hydroxide. When the crosslinking reaction has completed, the HA gel is washed repeatedly until the residual cross-linker was no longer detectable in the HA gel, At this point, the cross-linked gel is blended with 10% water in shear mode to create uniform and small particles. The blended cross-linked material reformulated with un-cross-linked materials HA for injectability and longevity.

The implants of the present invention further can be instilled, before or after implantation, with indicated medicines and other chemical or diagnostic agents. Examples of such agents include, but are not limited to, antibiotics, chemotherapies, other cancer therapies, brachytherapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

The present invention has been described particularly in connection with a breast, butt, or body implant, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Although the present invention has been described in relation to particular embodiments thereof, many other variations and modifications and other uses will become apparent to those skilled in the art. It is preferred, therefore, that the present invention be limited not by the specific disclosure herein, but only by the appended claims. The other methods, used for characterization of the products according to one embodiment are described in the following examples which illustrate preferred embodiments of one embodiment without, however, being a limitation thereof. Variations and modifications can, of course, be made without departing from the spirit and scope of the invention.

What is claimed is:

1. A method for cosmetic augmentation, comprising:
    modeling a 3D model of a human body and continuously updating a current shape of breast or butt from the 3D model to fit to a desired shape;
    forming a biocompatible cross-linked polymer having a multi-phase mixture with a time activated catalyst;
    injecting the mixture into a patient as a homogeneous fluid;
    after injection, activating the catalyst to cross-link the polymer after a predetermined period after injection into a patient; and
    augmenting soft tissue with the biocompatible cross-linked polymer.

2. The method of claim 1, comprising providing a predetermined controlled release of selected pharmaceutical substance to modulate soft tissue response to the polymer.

3. The method of claim 1, comprising cross-linking the polymer in a shell inside the patient.

4. The method of claim 1, wherein the polymer comprises one of: collagens, hyaluronic acids, celluloses, proteins, saccharides.

5. The method of claim 1, wherein the polymer comprises an extracellular matrix of a biological system.

6. The method of claim 1, comprising using cross linkers and forming homo-polymers or to form copolymers by crosslinking with other polymer species.

7. The method of claim 1, comprising adding a substance to the composition for biocompatibility.

8. The method of claim 1, comprising controlling drug releases at predetermined timing in anticipation of an onset of a negative physiological event in response to invading foreign bodies.

9. The method of claim 1, comprising fast releasing the composition.

10. The method of claim 1, comprising adding anesthetics, lidocaine or compound to reduce or eliminate acute inflammatory reactions to the pharmaceutical substance.

11. The method of claim 1, comprising adding one or more compositions selected from the group consisting of steroids, corticosteroids, dexamethasone, triamcinolone.

12. The method of claim 1, comprising providing a slow release substance to the pharmaceutical substance.

13. The method of claim 1, comprising providing an antiproliferative compound.

14. The method of claim 1, wherein the substance comprises paclitaxel, serolimas.

15. The method of claim 1, comprising controlling the scar formation process around a foreign body including capsular formation.

16. The method of claim 1, comprising providing a medium release to the pharmaceutical substance.

17. The method of claim 1, comprising optimizing degradation profile of the composition.

18. The method of claim 1, comprising minimizing migration of the composition.

19. The method of claim 1, comprising controlling an average molecular weight (Mn) and the polydispersity index.

20. The method of claim 1, comprising characterizing a target tissue, and maintaining a consistency of the composition in particle size and population densities.

21. The method of claim 1, comprising co-cross-linking glycosaminoglycan chemically with at least one other polymer including hyaluronan or hylan.

22. The method of claim 1, comprising adding a biodegradable surfactant or plasticizer to reduce surface tension of material as it is injected into a patient through a small diameter needle.

23. The method of claim 1, comprising injecting with a mechanical pump the biocompatible crosslinked polymer under soft tissue in a minimally invasive manner.

24. A method for cosmetic augmentation, comprising:
    modeling a 3D model of a human body and continuously updating a current shape of breast or butt from the 3D model to fit to a desired shape, forming a biocompatible cross-linked polymer having a multi-phase mixture with a predetermined controlled release of selected pharmaceutical substance to modulate soft tissue response to the polymer;

injecting the mixture into a patient and during or after injection, cross-linking the polymer in the patient;

filling a semi-permeable shell with the pharmaceutical substance; and augmenting soft tissue with the biocompatible cross-linked polymer.

* * * * *